under the bar code: US011150213B2

(12) United States Patent
Huang et al.

(10) Patent No.: US 11,150,213 B2
(45) Date of Patent: Oct. 19, 2021

(54) BIOLOGICAL OXYGEN DEMAND SENSORS

(75) Inventors: Zhen Huang, Newton, MA (US);
Patrick Kiely, Gatineau (CA);
Matthew Silver, Cambridge, MA (US);
Justin Buck, Cambridge, MA (US)

(73) Assignee: Cambrian Innovation Inc., Boston, MA (US)

( * ) Notice: Subject to any disclaimer, the term of this patent is extended or adjusted under 35 U.S.C. 154(b) by 1175 days.

(21) Appl. No.: 14/126,264

(22) PCT Filed: Jun. 14, 2012

(86) PCT No.: PCT/US2012/042501
§ 371 (c)(1),
(2), (4) Date: Jul. 10, 2014

(87) PCT Pub. No.: WO2012/174270
PCT Pub. Date: Dec. 20, 2012

(65) Prior Publication Data
US 2014/0353170 A1 Dec. 4, 2014

Related U.S. Application Data

(60) Provisional application No. 61/496,608, filed on Jun. 14, 2011.

(51) Int. Cl.
*G01N 27/416* (2006.01)
*G01N 27/327* (2006.01)
(Continued)

(52) U.S. Cl.
CPC ....... *G01N 27/4166* (2013.01); *G01N 27/327* (2013.01); *G01N 33/1806* (2013.01);
(Continued)

(58) Field of Classification Search
CPC ............... G01N 27/327; G01N 33/543; G01N 33/1806; G01N 33/1866; G01N 27/4166;
(Continued)

(56) References Cited

U.S. PATENT DOCUMENTS

| | | | |
|---|---|---|---|
| 4,090,940 | A | 5/1978 | Switzgable |
| 5,682,288 | A | 10/1997 | Wani |

(Continued)

FOREIGN PATENT DOCUMENTS

| | | |
|---|---|---|
| CN | WO 01/04626 A1 | 1/2001 |
| CN | 1364146 | 8/2002 |

(Continued)

OTHER PUBLICATIONS

Meyer et al., Applied and Enviornmental Microbiology, 2002, 1204-1210.*

(Continued)

*Primary Examiner* — Gurpreet Kaur
(74) *Attorney, Agent, or Firm* — Capitol Patent & Trademark Law Firm, PLLC

(57) ABSTRACT

Bioelectrochemical Systems (BES) for use as Biological Oxygen Demand (BOD) sensors, systems incorporating BES sensors for measuring BOD, and methods of using the sensors and systems for measuring BOD. The disclosed sensors are inexpensive to construct, long-lasting, have a fast response, and a large dynamic range. The invention includes biological oxygen demand (BOD) sensors which incorporate at least three working electrodes, at least one counter electrode, a reservoir for dilution fluid, and a sensor for measuring an electric current or a voltage which flows from the working electrodes to the counter electrode. The BOD sensors will typically also include at least one electrically active microbe disposed in proximity to the working electrode.

19 Claims, 6 Drawing Sheets

(51) Int. Cl.
*H01M 8/16* (2006.01)
*G01N 33/18* (2006.01)

(52) U.S. Cl.
CPC .......... *G01N 33/1866* (2013.01); *H01M 8/16* (2013.01); *Y02E 60/50* (2013.01)

(58) Field of Classification Search
CPC ......... C12Q 1/00; Y02E 60/527; Y02E 60/50; H01M 8/16
See application file for complete search history.

(56) References Cited

U.S. PATENT DOCUMENTS

| | | | |
|---|---|---|---|
| 6,114,172 A * | 9/2000 | Siepmann | G01N 33/1806 436/62 |
| 6,270,649 B1 * | 8/2001 | Zeikus | C12N 13/00 205/413 |
| 8,440,438 B2 | 5/2013 | Cheng et al. | |
| 2001/0003276 A1 | 6/2001 | De Souza et al. | |
| 2004/0040868 A1 | 3/2004 | DeNuzzio et al. | |
| 2005/0164331 A1 | 7/2005 | Kim et al. | |
| 2005/0183964 A1 | 8/2005 | Roberts et al. | |
| 2005/0255345 A1 | 11/2005 | Gerritse et al. | |
| 2008/0138663 A1 | 6/2008 | Kubo et al. | |
| 2009/0130734 A1 | 5/2009 | Mets | |
| 2009/0142627 A1 | 6/2009 | Shimomura et al. | |
| 2009/0305084 A1 | 12/2009 | Crookes et al. | |
| 2010/0040908 A1 * | 2/2010 | Nealson | H01M 8/16 429/2 |
| 2010/0175821 A1 | 7/2010 | Cho et al. | |
| 2010/0203359 A1 * | 8/2010 | Borole | C12N 1/20 429/2 |
| 2010/0267161 A1 | 10/2010 | Wu et al. | |
| 2011/0165667 A1 | 7/2011 | Mets | |
| 2013/0011696 A1 * | 1/2013 | Wallin | H01M 8/16 429/2 |
| 2013/0112601 A1 * | 5/2013 | Silver | C02F 3/025 210/143 |
| 2013/0319940 A1 | 12/2013 | Josse et al. | |

FOREIGN PATENT DOCUMENTS

| | | |
|---|---|---|
| CN | 101620201 | 1/2010 |
| CN | 101849180 A | 9/2010 |
| CN | 102351310 | 2/2012 |
| DE | 44 20 571 A1 | 12/1995 |
| EP | 0242225 A2 | 10/1987 |
| EP | 573226 A1 | 12/1993 |
| EP | 0667521 A1 | 8/1995 |
| JP | 57-022551 | 2/1982 |
| JP | 05-010921 B2 | 1/1993 |
| JP | 08138978 A | 5/1996 |
| JP | H08136498 | 5/1996 |
| JP | H10-230293 A | 9/1998 |
| JP | 11-010184 | 1/1999 |
| JP | H11-216496 A | 8/1999 |
| JP | H11-253993 A | 9/1999 |
| JP | 2000-024687 A | 1/2000 |
| JP | 2000-051894 A | 2/2000 |
| JP | 2000-126794 A | 5/2000 |
| JP | 2000-157995 A | 6/2000 |
| JP | 2001-145896 A | 5/2001 |
| JP | 2002-086189 A | 3/2002 |
| JP | 2002-520032 A | 7/2002 |
| JP | 2005-125172 A | 5/2005 |
| JP | 2006-35158 | 2/2006 |
| JP | 2007-117995 A | 5/2007 |
| JP | 2007-227216 A | 9/2007 |
| JP | 2008-114191 A | 5/2008 |
| JP | 2009-222667 A | 10/2009 |
| JP | 2009-258024 A | 11/2009 |
| WO | WO-200003447 A1 | 1/2000 |
| WO | WO2003097861 | 11/2003 |
| WO | WO-2004004036 A2 | 1/2004 |
| WO | WO-2008059331 A2 | 5/2008 |
| WO | WO-2008103028 A1 | 8/2008 |
| WO | WO-2009042631 A2 | 4/2009 |
| WO | WO-2009072887 A1 | 6/2009 |
| WO | WO-2009131452 A1 | 10/2009 |
| WO | WO-2009155587 A2 | 12/2009 |
| WO | WO-2010044983 A2 | 4/2010 |
| WO | WO-2010147683 A1 | 12/2010 |
| WO | WO-2011000084 A1 | 1/2011 |
| WO | WO-2011003081 A1 | 1/2011 |
| WO | WO 2011/072065 | 6/2011 |
| WO | WO-2012011984 A1 | 1/2012 |

OTHER PUBLICATIONS

Tront et al., Biosensors and Bioelectronics, 2008, 586-590.*
Kim et al. Biotechnology Letters, 541-545, 2003.*
Larsen et al., Anal. Chem, 1997, 69, 3527-3531.*
Chang et al., Biosensor and Bioelectronics 2004, 607-613 (Year: 2004).*
Arnold, et al., "Regulation of Dissimilatory Fe(III) Reduction Activity in *Shewanella putrefaciens*," *App and Env Microbiol*, vol. 56, No. 9, pp. 2811-2817 (Sep. 1990).
BCC Research, "Environmental Sensing and Monitoring Technologies: Global Markets," a BCC Research Instrumentation & Sensors Report, Oct. 2011 (IAS030B) (5 pgs.).
Beliaev, et al., "Global transcriptome analysis of Shewanella oneidensis MR-1 exposed to different terminal electron acceptors," *J Bacteriol*, vol. 187, No. 20, pp. 7138-7145 (Oct. 2005).
Biffinger, et al., "A Biofilm Enhanced Miniature Microbial Fuel Cell Using Shewanella Oneidensis DSP10 and Oxygen Reduction Cathodes," *Biosensors and Bioelectronics*, vol. 22, pp. 1672-1679 (2007).
Bourgeois, et al., "On-Line Monitoring of Wastewater Quality: A Review," *Journal of Chemical Technology & Biotechnology*, vol. 76, pp. 337-348 (2001).
Bretschger, et al., "Current Production and Metal Oxide Reduction by Shewanella oneidensis MR-1 Wild Type and Mutants," *App and Env Microbiol*, vol. 73, No. 21, pp. 7003-7012 (2007), including "Erratum," *App and Env Microbiol*, vol. 74, No. 2, pp. 553 (2008); 11 pages.
Chang, et al., "Improvement of a microbial fuel cell performance as a BOD sensor using respiratory inhibitors," *Biosensors and Bioelectronics*, vol. 20, pp. 1856-1859 (2005).
Chang, et al., "Continuous determination of biochemical oxygen demand using microbial fuel cell type biosensor," *Biosensors and Bioelectronics*, vol. 19, pp. 607-613 (2004).
Cheng, et al., "Direct Biological Conversion of Electrical Current into Methane by Electromethanogenesis," Environmental Science and Technology, American Chemical Society, vol. 43, No. 10, pp. 3953-3958 (Mar. 26, 2009).
Extended European Search Report issued by the European Patent Office for European Application No. 10836646.9 dated Jun. 10, 2015 (6 pgs.).
Cruz-Garcia, et al., "Respiratory nitrate ammonification by Shewanella oneidensis MR-1," *J Bacteriol*, vol. 189, No. 2, pp. 656-662 (Jan. 2007).
David, et al., "Nitrogen balance in and export from an agricultural watershed," *J Environ Qual.*, vol. 26, pp. 1038-1048 (1997).
Dichristina, T.J., "Effects of Nitrate and Nitrite on Dissimilatory Iron Reduction by *Shewanella putrefaciens*," J Bacteriol, vol. 174, No. 6, pp. 1891-1896 (1992).
Di Lorenzo, et al., "A single-chamber microbial fuel cell as a biosensor for wastewaters," Water Research, vol. 43, pp. 3145-3154 (2009).
Dinnes, et al., "Nitrogen Management Strategies to Reduce Nitrate Leaching in Tile-Drained Midwestern Soils," *Agronomy Journal*, vol. 94, pp. 153-171 (2002).
Du, et al., "A State of the Art Review on Microbial Fuel Cells: A Promising Technology for Wastewater Treatment and Bioenergy," Biotechnology Advances, vol. 25, pp. 464-482 (2007).
European Supplemental Search Report issued by the European Patent Office for European Patent Application No. EP12800665.7 dated Mar. 10, 2015 (6 pages).

(56) References Cited

OTHER PUBLICATIONS

Extended European Search Report issued by the European Patent Office for European Application No. 10789884.3 dated May 16, 2013 (10 pgs.).
Faeth, P., "Fertile Ground: Nutrient Trading's Potential to Cost-Effectively Improve Water Quality," Washington, DC: World Resources Institute, 59 pgs. (2000).
Gieling, et al., "ISE and Chemfet sensors in greenhouse cultivation," *Sensors and Actuators B*, vol. 105, pp. 74-80 (2005).
Gorby, et al., "Electrically conductive bacterial nanowires produced by Shewanella oneidensis strain MR-1 and other microorganisms." *Proceedings of the National Academy of Sciences*, vol. 103, No. 30, pp. 11358-11363 (2006).
Grommen, et al., "Removal of Nitrate in Aquaria by Means of Electrochemically Generated Hydrogen Gas as Electron Donor for Biological Denitrification," *Aquacultural Engineering*, vol. 34, No. 1, pp. 33-39 (2006).
Holmes, "Potential Role of a Novel Psychrotolerant Member of the Family Geobacteraceae, Geopsychrobacter electrodiphilus gen. nov., sp. nov., in Electricity Production by a Marine Sediment Fuel Cell," *Applied and Environmental Microbiology*, vol. 70, No. 10 pp. 6023-6030 (Oct. 2004).
International Search Report and Written Opinion issued by the Korean Intellectual Property Office as International Searching Authority for International Application No. PCT/US2010/025224 dated Oct. 12, 2010 (10 pgs.).
International Search Report and Written Opinion issued by the Korean Intellectual Property Office as International Searching Authority for International Application No. PCT/US2010/059554 dated Sep. 26, 2011 (8 pgs.).
International Search Report and Written Opinion issued by the U.S. Patent and Trademark Office as International Searching Authority for International Application No. PCT/US2012/042501 dated Sep. 28, 2012 (10 pgs.).
Jia, et al., "Simultaneous Organics Removal and Bio-Electrochemical Denitrification in Microbial Fuel Cells," *Bioprocess and Biosystems Engineering*, vol. 31, No. 4, pp. 315-321 (2008).
Kim, et al., "A Microbial Fuel Cell Type Lactate Biosensor Using a Meal-Reducing Bacterium, Shewanella Putrefaciens," J. Microbiol. Biotechnol., vol. 9, No. 3, pp. 365-367 (1999).
Kang, et al., "A microbial fuel cell with improved cathode reaction as a low biochemical oxygen demand sensor," *Biotechnology Letters*, vol. 25, pp. 1357-1361 (2003).
Rabaey, et al., "Microbial fuel Cells: Novel Biotechnology for Energy Generation," Trends in Biotechnolgy, vol. 23, No. 6, pp. 291-298 (2005).
Kim, et al., "Membrane-electrode assembly enhances performance of a microbial fuel cell type biological oxygen demand sensor," *Environmental Technology*, vol. 30, No. 4, pp. 329-336 (Apr. 1, 2009).
Kim, et al., "Microbial Fuel Cell-type Biochemical Oxygen Demand Sensor," Encyclopedia of Sensors, vol. 6, pp. 127-138 (2006).
Kim, et al., "Novel BOD (biological oxygen demand) sensor using mediator-less microbial fuel cell," *Biotechnology Letters*, vol. 25, pp. 541-545 (2003).
Kostka, J.E. and Nealson, K.H., "Dissolution and reduction of magnetite by bacteria," *Environmental Science and Technology*, vol. 29, pp. 2535-2540 (1995).
Kumlanghan, et al., "Microbial fuel cell-based biosensor for fast analysis of biodegradable organic matter," *Biosensors and Bioelectronics*, vol. 22, pp. 2939-2944 (2007).
Kuroda, et al., "CO2 Reduction to Methane and Acetate Using a Bio-electro Reactor with Immobilized Methanogens and Homoacetogens on Electrodes," Energy Conversion and Management, vol. 36, No. 6-9, pp. 787-790 (1995).
Liu, et al., "Immobilised Activated Sludge Based Biosensor for Biochemical Oxygen Demand Measurement," *Biosensors and Bioelectronics*, vol. 14, No. 12, pp. 883-893 (2000).
Liu, J. and Mattiasson, B., "Microbial BOD Sensors for Wastewater Analysis," *Water Research*, vol. 36, No. 15, pp. 3786-3802 (2002).

Logan, Bruce E, and Regan, John M., "Microbial Fuel Cells: Challenges and Applications." *Environmental Science & Technology*, vol. 40, No. 17, pp. 5172-5180 (Sep. 1, 2006).
Tabacova, et al., "Maternal Exposure to Exogenous Nitrogen Compounds and Complications of Pregnancy," Archives of Environmental Health: An International Journal, vol. 52, No. 5, pp. 341-347 (1997).
Bendikov, et al., "Development and Environmental Application of a Nitrate Selective Microsensor Based on Doped Polypyrrole Films," Sensors and Actuators B, vol. 106, No. 2 (May 13, 2005), 7 pages.
Bergel, et al., "Catalysis of Oxygen Reduction in PEM Fuel Cell by Seawater Biofilm." Electrochem. Commun., vol. 7(9), pp. 900-904 (2005).
Call, D. and Logan, B. E., "Hydrogen production in a single chamber microbial electrolysis cell lacking a membrane," Environ. Sci. Technol., vol. 42, pp. 3401-3406 (2008).
Cheng, et al., "Increased Performance of Single-Chamber Microbial Fuel Cells Using an Improved Cathode Structure," Electrochemistry Communications, vol. 8, No. 3, pp. 489-494 (Mar. 2006).
Cheng, S. and Logan, B.E., "Sustainable and Efficient Biohydrogen Production via Electrohydrogenesis," PNAS, vol. 104, No. 47, pp. 18871-18873 (2007).
Clauwaert, et al., "Open Air Biocathode Enables Effective Electricity Generation with Microbial Fuel Cells," Environmental Science & Technology, vol. 41, No. 21, pp. 7564-7569 (Nov. 2007).
Freguia, et al., "Electron and Carbon Balances in Microbial Fuel Cells Reveal Temporary Bacterial Storage Behavior During Electricity Generation," Environmental Science & Technology, vol. 41, No. 8, pp. 2915-2921 (Apr. 2007).
Hallenbeck, P.C. and Benemann, J.R., "Biological hydrogen production; fundamentals and limiting processes." Int. J. Hydrogen Energy, vol. 27, pp. 1185-1193 (2002).
He, et al., "Electricity Generation from Artificial Wastewater Using an Upflow Microbial Fuel Cell," Environmental Science & Technology, vol. 39, No. 14, pp. 5262-5267 (Jul. 2005).
He, Zhen, and Angenent, L.T., "Application of Bacterial Biocathodes in Microbial Fuel Cells," Electroanalysis, vol. 18, No. 19-20, pp. 2009-2015 (Oct. 2006).
Lee, et al., "Fate of H2 in an Upflow Single-Chamber Microbial Electrolysis Cell Using a Metal-Catalyst-Free Cathode," Environmental Science & Technology, vol. 43, No. 20, pp. 7971-7976 (Oct. 15, 2009).
Liu, et al., "Production of Electricity during Wastewater Treatment Using a Single Chamber Microbial Fuel Cell." Environmental Science & Technology, vol. 38, No. 7, pp. 2281-2285 (2004).
Vitousek, et al., "Human Alteration of the Global Nitrogen Cycle: Sources and Consequences," Ecological Applications, vol. 7, pp. 737-750 (1997).
Logan, et al., "Electricity generation from cysteine in a microbial fuel cell," Water Res., vol. 39, pp. 942-952 (2005).
Logan, et al., "Graphite Fiber Brush Anodes for Increased Power Production in Air-Cathode Microbial Fuel Cells," Environmental Science & Technology, vol. 41, No. 9, pp. 3341-3346 (May 2007).
Logan, et al., "Microbial Electrolysis Cells for High Yield Hydrogen Gas Production from Organic Matter," Environmental Science & Technology, vol. 42, No. 23, pp. 8630-8640 (Dec. 2008).
Min, et al., "Electricity Generation from Swine Wastewater Using Microbial Fuel Cells," Water Research, vol. 39, No. 20, pp. 4961-4968 (Dec. 2005).
Niessen, et al., "Gaining Electricity from in Situ Oxidation of Hydrogen Produced by Fermentative Cellulose Degradation," Letters in Applied Microbiology, vol. 41, No. 3, pp. 286-290 (Sep. 2005).
Oh, S., and Logan, B.E., "Hydrogen and Electricity Production from a Food Processing Wastewater Using Fermentation and Microbial Fuel Cell Technologies," Water Research, vol. 39, pp. 4673-4682 (2005).
Pham, et al., "Microbial Fuel Cells in Relation to Conventional Anaerobic Digestion Technology," Engineering in Life Sciences, vol. 6, No. 3, pp. 285-292 (2006).
Rabaey, et al., "Biofuel Cells Select for Microbial Consortia That Self-Mediate Electron Transfer," Applied and Environmental Microbiology, vol. 70, No. 9, pp. 5373-5382 (Sep. 2004).

(56) References Cited

OTHER PUBLICATIONS

Rabaey, et al., "Tubular Microbial Fuel Cells for Efficient Electricity Generation," Environmental Science and Technology, vol. 39, No. 20, pp. 8077-8082 (2005).

Rabaey, et al., "Cathodic Oxygen Reduction Catalyzed by Bacteria in Microbial Fuel Cells," The ISME Journal, pp. 1-9 (Feb. 2008).

Rozendal, et al., "Principle and Perspectives of Hydrogen Production through Biocatalyzed Electrolysis," International Journal of Hydrogen Energy, vol. 31, No. 12, pp. 1632-1640 (Sep. 2006).

Selembo, et al., "The Use of Stainless Steel and Nickel Alloys as Low-Cost Cathodes in Microbial Electrolysis Cells," Journal of Power Sources, vol. 190, No. 2, pp. 271-278 (May 2009).

Van Ginkel, et al., "Biohydrogen gas production from food processing and domestic wastewaters," Int. J. Hydrogen Energy, vol. 30, pp. 1535-1542 (2005).

Zhang, Y. and Angelidaki, I., "Submersible microbial fuel cell sensor for monitoring microbial activity and BOD in groundwater: Focusing on impact of anodic biofilm on sensor applicability," Biotechnology and Bioengineering, 34 pgs. (2011).

Ratako, et al., "Micro- and Mini-nitrate Sensors for Monitoring of Soils, Groundwater and Aquatic Systems," Center for Embedded Network Sensing, 3 pgs. (May 12, 2009).

Ringeisen, et al., "High Power Density from a Miniature Microbial Fuel Cell Using Shewanella oneidensis DSP10," Environ. Sci. Technol., vol. 40, pp. 2629-2634 (2006).

Shantaram, et al., "Wireless sensors powered by microbial fuel cells," *Environ Sci Technol*, vol. 39, pp. 5037-5042 (2005).

Sukkasem, et al., "Effect of Nitrate on the Performance of Single Chamber Air Cathode Microbial Fuel Cells," *Water Research*, vol. 42, pp. 4743-4750 (2008).

Tabacova, et al., "Exposure to Oxidized Nitrogen: Lipid Peroxidation and Neonatal Health Risk," *Archives of Environmental Health: An International Journal*, vol. 53, No. 3, pp. 214-221 (1998).

Anonymous: "BSB-Fibel Bestimmung des Biochemischen Sauerstoffbedarfs", Apr. 22, 2003, Retrieved from the Internet: URL: http://old.omnilab.de/hpb/export/1/BSBD.pdf, p. 20, p. 38-p. 47.

* cited by examiner

BIOLOGICAL OXYGEN DEMAND SENSORS

RELATED APPLICATIONS

This application is a national-stage entry of International Patent Application No. PCT/US2012/042501, filed 14 Jun. 2012, which claims the benefit of U.S. Provisional Application No. 61/496,608, filed Jun. 14, 2011, which is incorporated by reference herein in its entirety.

FIELD OF THE INVENTION

The invention relates to biological oxygen demand (BOD) sensors. BOD sensors may be used, for example, to monitor organic pollutants in water.

BACKGROUND

Biochemical oxygen demand (BOD) is the amount of dissolved oxygen needed by aerobic biological organisms in a fluid (typically water) to break down the organic materials present. BOD is typically expressed as the amount of oxygen needed for a given fluidic sample, at a given temperature, over a given time period. Because BOD relates to biological activity, a quoted BOD value is not very precise, however it gives an good indication of the organic content of the fluid.

BOD measurements are most often used to monitor the organic content of water, e.g., waste water, industrial process water, agricultural process water, agricultural run-off, surface water. While organics in the water can come from a number of "natural" sources, e.g., aquatic plants or fallen leaves, organics in the water are most often the result of contamination from animal waste or industrial processes using chemicals. Organic contamination may also include, for example, food processing waste, hydrocarbons, personal care products, or insecticides. Thus, measuring the BOD of water gives a general sense of the cleanliness of the water and its potability. Some organic compounds, such as volatile fatty acids (VFAs), are exclusively correlated with animal wastes and signal the potential presence of dangerous microorganisms (e.g., cholera). Most facilities, required to monitor water quality regularly, measure BOD along with suspended solids and ammonia content.

Current practice for monitoring BOD in wastewater treatment processes and industry requires the $BOD_5$ test, named for the five days required to obtain a result. Because it requires five days to administer, there are significant delays between taking the sample and acquisition of a BOD measurement, making real-time monitoring impossible. Additionally, the $BOD_5$ test suffers from questionable accuracy and irreproducibility while being time- and labor-intensive. See, DiLorenzo et al., *Water Research*, 43 (2009) 3145-3154, incorporated by reference herein in its entirety.

Consequently, there is substantial interest in improved real-time sensors for BOD monitoring. Such sensors will greatly benefit the overall approach to water management by allowing more rapid adjustment to developing conditions while reducing costs. The ideal sensor is inexpensive, robust, accurate, and has a large range of sample concentrations for which the sensor is effective.

SUMMARY

The invention provides improved BOD sensors, suitable for use in monitoring the quality of waste process water, industrial process water, and agricultural process water, among others uses. The invention includes sensors, systems including the sensors, methods of using the sensors to measure BOD, and dilution fluids for use with the systems of the invention. The sensors are superior to prior BOD sensors in that they are inexpensive, robust, have a fast response to BOD changes, and are able to detect a wide range of BOD.

The invention includes biological oxygen demand (BOD) sensors which incorporate at least three working electrodes, at least one counter electrode, a reservoir for dilution fluid, and a sensor for measuring an electric current or a voltage which flows from the working electrodes to the counter electrode. The BOD sensors will typically also include at least one electrically active microbe disposed in proximity to the working electrode. BOD sensors of the invention may additionally include mixing chambers to receive a sample to be monitored for BOD, wherein the sample is diluted to make at least three different dilutions, all of which are measured for BOD. By measuring the BOD for at least three samples it is possible to quickly establish a BOD value, while still maintaining an ability to measure a wide range of BOD values. In some embodiments of the invention, a voltage source is operatively coupled between the working electrodes and the counter electrode.

The invention includes methods for determining the biological oxygen demand (BOD) of a sample, comprising diluting the sample with a dilution fluid to obtain at least three different dilutions of the sample, measuring the BOD of each of the at least three different dilutions using a bioelectrochemical system (BES) to obtain at least three BOD values, and comparing the at least three BOD values to determine a BOD of the sample. The measurement procedure will typically entail correlating a current or voltage measurement from the BES to a BOD value, for example by reference to a calibration curve for the BES. In an embodiment, the method is completed in less than 1 hour.

The invention includes another type of sensor for determining the presence of targeted organic compounds. This sensor includes first and second electrodes, a voltage source operably coupled to the first and second electrodes, a current sensor operably coupled to the first and second electrodes and capable of measuring a current between the first and second electrodes, and a culture of exoelectrogenic bacteria whose capacity to metabolically utilize organic materials as an electron donor is substantially limited to the targeted organic compounds. In an embodiment, this sensor additionally includes a housing for the first and second electrodes, wherein the housing limits aerobic metabolism in proximity to the first electrode or the second electrode. The sensor may use an exoelectrogenic bacteria such as *Geobacter sulfurreducens*. This sensor will be very useful for measuring volatile fatty acids, such as found in municipal waste water and anaerobic digesters.

The invention additionally includes bioelectrochemical systems (BES) utilizing one or more electrode pairs capable of real-time sensing and monitoring of BOD, including VFAs and other complex organics. The system can operate using a single electrode pair as a sensor or multiple electrode pairs as a sensor array. Where multiple BESs are used, they can be capable identifying the minimum dilution to achieve sub-saturation conditions utilizing a series of dilutions, typically prepared with a buffered dilution fluid. This approach minimizes sensor response time because it uses instantaneous current as signal. This approach also avoids pH and salinity concerns because the sample is buffered. Furthermore, the series of dilutions assure that at least one sensor is not saturated in most situations and that the sensor will have greater accuracy over a longer period without calibration.

The invention also includes a system for measuring the oxygen demand of a fluid, comprising a bioelectrochemical system (BES), a dilution solution mixing system coupled to a sample, an electric current or voltage sensor operably coupled to the BES, and control electronics operably connected to the current or voltage sensor and the buffer injection system, and capable of receiving a measurement from the current or voltage sensor and causing the buffer mixing system to contact the sample with a buffer.

DETAILED DESCRIPTION

The invention provides sensors, systems, and methods for measuring the biological oxygen demand (BOD) of a fluid, for example, water. The sensors are fast, inexpensive, robust, and have a large dynamic range for measuring BOD in a sample. The sensors will allow real-time measurement of BOD for a number of applications, including wastewater treatment, industrial process water treatment, agricultural process water treatment, and surface water monitoring.

Bioelectrochemical Systems (BES)

The BOD sensors of the invention are based on bioelectrochemical systems (BES), such as microbial fuel cells. BESs are novel devices that use electrically active microbes, (often referred to interchangeably as, electrogens, electricigens or exoelectrogens), to generate electricity in a fuel cell (anode, cathode, permeable barrier), or quasi fuel cell (two electrodes), architecture. Typically, the electrically active microbes require a nutrient or substrate (e.g., a chemical species) to complete certain metabolic processes. During this metabolic process, the electrically active microbe will donate electrons to an electrode of a circuit or receive electrons from a circuit resulting in a measurable change in electrical potential or electric current within the circuit. Because BESs can use a diverse range of organics as nutrients, BES output will vary as a function of the BOD loading rate as well as the type of organic nutrient.

The present invention offers multiple arrangements of BESs which are capable of detecting and measuring the total BOD, including VFA, or VFA alone, by determining the current produced by the metabolic activity of electrochemically active microbe community. Typically, the organic materials are oxidized at one electrode (e.g., the anode) in the presence of the electrogen community, which acts as a catalyst. In this arrangement, electrons flow from the anode to a second electrode (e.g., the cathode), thereby generating current. The current may be measured directly, or it can be measured resistively as a potential.

Figure 1:
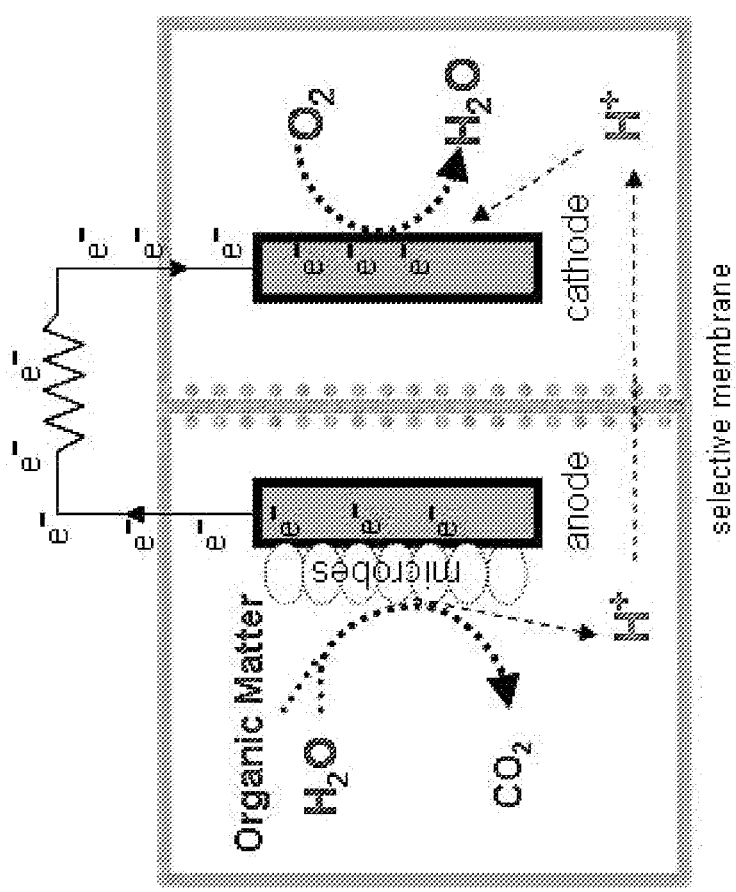
FIG. 1 depicts an exemplary microbial fuel cell.

Microbial fuel cells (MFCs), a type of BESs, have been used to report on concentrations of biological oxygen demand (BOD). An exemplary microbial fuel cell (MFC) is shown in FIG. 1. The MFC comprises two electrodes, i.e., an anode and a cathode, electrically active microbes, a selective membrane, e.g., a proton permeable membrane, and circuitry connecting the anode and cathode. At the anode side of the MFC, microbes metabolize organic matter, using water, to produce carbon dioxide and protons. During this process, electrons ($e^-$) are produced which are donated to the electrode (e.g., the anode). As shown in FIG. 1, the donated electrons may travel through a circuit to another electrode (e.g., the cathode) where the electrons are donated to oxygen to produce water. However, as is known in the art, a multitude of cathode arrangements are available using a number of species. The cathode could be, for example, exposed to the air. As shown in FIG. 1, protons can travel through the semi-permeable membrane to balance the charge with the electrons flowing across the circuit.

As shown in FIG. 1, an MFC can generate an electric current as a consequence of the presence of nutrients (or substrates) which are metabolized by the microbes. Surprisingly, a wide variety of microbes are capable of donating electrons to electrodes as a consequence of metabolism. The nutrients can be organic compounds (sugars, carbohydrates, small organic acids) or nitrates, or more exotic species. The specific microbes are discussed in more detail below. In the exemplary MFC shown in FIG. 1, when organic matter is present, and the conditions are correct, an electric current is produced between the electrodes. The same metabolic processes can be harnessed to produce a sensor, however, by measuring a current flow or potential as the MFC is exposed to differing fluidic media with varying levels of the needed nutrients. Alternatively, the cell arrangement shown in FIG. 1 may be biased with an external power source (not shown), and the potential monitored to determine when metabolic activity is taking place, and thus correlating with the presence of the nutrients. In some embodiments, the selective membrane is not needed to perform the sensing.

Using an MFC as disclosed in FIG. 1 presents a number of challenges in real-world applications. Specifically, for in-line industrial applications, MFC sensors suffer from: (1) An inability to provide both short response time and large dynamic range; (2) low reproducibility and stability; and (3) substantial variations in measured BOD as a function of organic composition. See, Kim et al., *Biotechnology Letters*, 25 (2003) 541-545, incorporated herein by reference in its entirety.

The problems noted above have been substantially solved with the disclosed invention. That is, the sensors, systems, and methods of the invention provide a BOD sensor with a fast response and large dynamic range, wherein the values are reproducible and stable. As disclosed in FIG. 2, the invention solves the response time and dynamic range issues by providing multiple parallel BES sensors, each of which monitors a separately diluted stream of sample for BOD.

Figure 2:
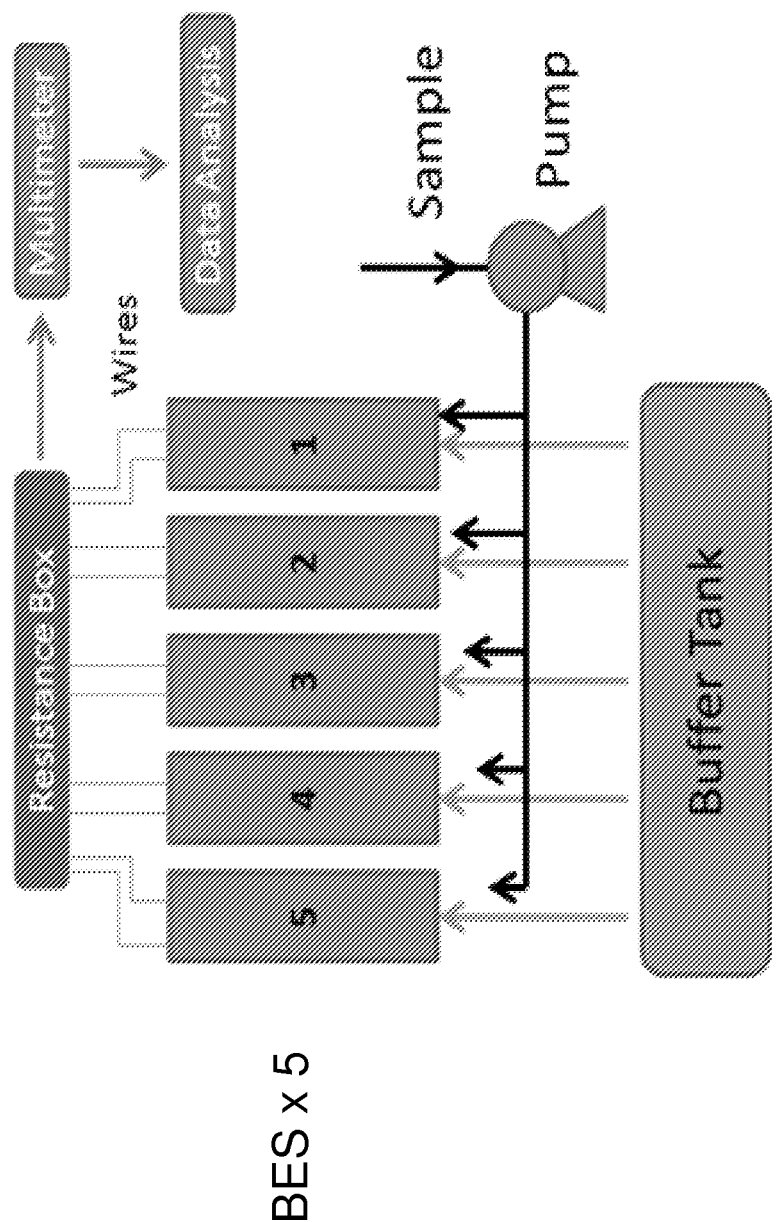
FIG. 2 is schematic diagram of an embodiment of a biological oxygen demand sensor of the invention.

FIG. 2 represents an embodiment of the invention, however alternative arrangements of the components (e.g., number of cells, type of electrical measurement) will be evident to those of skill in the art. As shown in FIG. 2, the sensor system comprises multiple BES cells, a buffer tank (dilution fluid reservoir), a pump (e.g., a peristaltic pump), a resistance box, and a multimeter or other sensor capable of measuring voltage and/or current. In an embodiment, each BES cell is substantially identical. During measurement, each cell receives some amount of a sample, and a current or voltage is measured in each cell to determine a value for BOD. In some embodiments, one cell will receive an undiluted sample, while the remaining cells will receive alternatively diluted samples. The dilutions may be prepared by consistently flowing dilution fluid (e.g., buffer) at a constant rate into each cell and metering an amount of sample such that alternative concentrations of sample are created. Alternatively, the dilutions may be created by mixing (contacting) differing amounts of dilution fluid with the same amount of sample. Alternatively, a first dilution may be serially diluted to produce a range of diluted samples.

The dilution fluid may be any fluid that is compatible with the microbes and electrodes The dilution fluid will preferably have an ionic strength (conductivity) greater than the sample (e.g., a dilution fluid comprised of a buffered saline solution with a sufficiently high salinity). The dilution fluid will typically be buffered with a weak acid or a weak base and contain a suitable counter ion to maintain the buffered conditions as the sample properties fluctuate. In an embodiment, the conductivity of the dilution fluid is at least about 20 millisiemens, e.g., at least about 50 millisiemens, e.g., at least about 100 millisiemens, e.g., at least about 200 millisiemens, e.g., at least about 500 millisiemens. The dilution fluid may also contain nutrients needed to keep the microbes functioning optimally, e.g., sugars, amino acids, electrolytes, sources of nitrogen, sources of phosphorous, sources of sulfur.

The sample that is analyzed by a system of the invention may be from any of a number of processes, as outlined in the background section. Additionally, the entire sample may be diluted before it is introduced to a system of the invention, wherein it will undergo further dilution. While FIG. 2 discloses a pump, it is additionally possible that the pump is replaced by the actions of an operator, who prepares separate dilutions of a sample and introduces the samples to the multiple cells to thereby determine the BOD.

As discussed in greater detail below, each BES cell will be calibrated prior to operation so that a given current or voltage may be correlated to a given level of BOD. The response of a BES may be modified by altering the size/shape of the cell, the size/shape of the electrode, the flow rate, or the microbial density of the cell. Thus, it is possible to tune each BES cell to achieve a beneficial linear range throughout which current (or potential) may be correlated to a BOD level. Additionally, because each cell is tuned for greater performance for a given BOD level, the dynamic range of the system can be made large by including a number of cells with different properties operating in parallel. Because each cell will operate in linear mode, the responsivity will also be high. That is, a change in BOD level will quickly result in a change in measured current (or potential) for at least one of the BESs, allowing a change in BOD to be quickly recognized. Thus, the sensors will allow real-time monitoring of BOD.

While not shown in FIG. 2, a system of the invention may include a processor which will receive values from the multimeter, for example, for each BES cell. The processor will compare the values from the multimeter to a previously-measured correlation between BOD and current/potential for each BES cell, and assign a BOD value. In an embodiment, the processor may simply output the calculated BOD value, e.g., to a display. In an embodiment, the processor will determine if the measured current/potential is outside of the linear range (e.g., below measurement threshold or saturated) and output a null value for that cell (e.g., NV, Err, N/A, etc.). In an embodiment, the processor will only output a BOD value for the one or more cells which have a current/potential measurement in the linear range. In an embodiment, the processor will average the values of the measurements for the one or more cells which have a current/potential measurement in the linear range and then output an average value. The processor may also use rate of change information for one or more cells to determine that a change in BOD levels has occurred, and thus restart a measurement algorithm.

While a multimeter is displayed in FIG. 2, one of skill would be able to use any of a number of current or potential (e.g., voltage) sensors to measure a change in the electrical properties of a BES cell. For example, a sensor may comprise a voltmeter, an ammeter, electrometer, ohmmeter, or a potentiometer. Non-traditional methods of measuring current or potential are also envisioned, for example measuring a temperature change in a resistive system as a response to increased current, or measuring the luminosity of an LED that receives current from the system.

In the embodiment shown in FIG. 2, the sensor array system contains five identical cells. Each cell shares a common buffer supply tank, but contains its own anode and cathode chambers. The linear relationship of current with BOD for each cell will be demonstrated and confirmed before the five cells work in parallel. The feed for each cell will be a mixture of buffer solution with a fixed flow rate, and sample with different flow rate to make various dilutions. The mixture of buffer solution and sample will be pumped into each cell continuously. The amount of sample pumped into each cell will be controlled by flow rate in such way that each cell will contain sample diluted by a predetermined amount of buffer. For example, in a five electrode pair system, the ratio of flow rate for cell 1, 2, 3, 4, 5 can be 1:0.5:0.25:0.125:0.075 so that the sample can diluted to 1, 2, 4, 8, 16 times, respectively. The benefit of series dilution is that the minimum dilution rate can be identified to enhance the accuracy.

While FIG. 2 shows separate cells having their own electrodes, it is contemplated that alternative electrode arrangements could be used. For example, two or more BES cells could share a common electrode, e.g., a common cathode. The electrode may be constructed from any of a number of materials (metals, plastic, etc.). In some embodiments, the anodes comprise carbon fibers, e.g., carbon wire, and the cathodes comprise stainless steel, e.g., stainless steel wire. The electrodes may be made of any shape, for example foils, bars, squares, buttons, etc. In an embodiment the electrodes are made from a mesh material, e.g., an open mesh (screen-like) material, allowing passage of fluids past the electrodes.

Figure 3B:
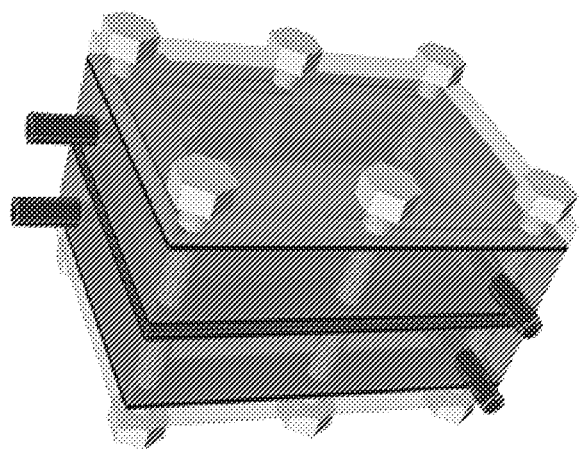
FIG. 3B depicts an embodiment of a bioelectrochemical system for use in a BOD sensor.
Figure 3A:
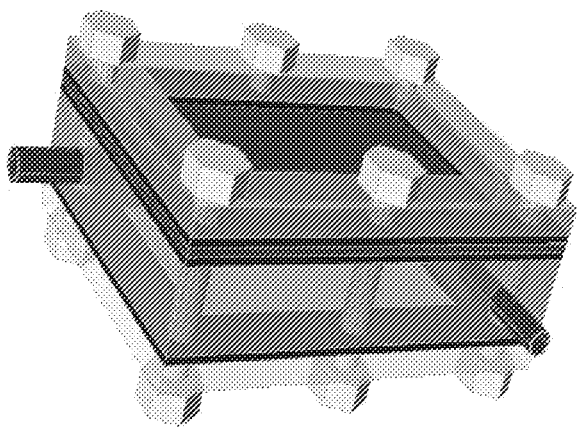
FIG. 3A depicts an embodiment of a bioelectrochemical system for use in a BOD sensor.

Specific designs for the BES cells are shown in FIGS. 3A and 3B. Both FIG. 3A and FIG. 3B comprise a flow-cell chamber with an internal anode. The sample, or diluted sample, will flow in one port and out the other. As shown in FIGS. 3A and 3B, the anodes will be constructed from carbon fiber mesh. The cell in FIG. 3A uses an air cathode, while the cell in FIG. 3B has flow cell anodes and cathodes, similar to the traditional microbial fuel cell design. In both FIG. 3A and FIG. 3B a semi-permeable membrane is present between the anode and cathode, however in FIG. 3A the membrane is external (exposed to air) while in FIG. 3B the membrane is internal and between the two flow cells. The cell in FIG. 3B may be operated with and oxygenated fluid, e.g., oxygenated water, or it may be used as an air cathode by passing air through the cell, e.g., with a pump, compressed air, or a slight vacuum on one side.

Applied Current

In one aspect of the invention current is applied to the system. In another aspect, current is not applied to the system. The preferred potential applied is approximately 0.8V. The system can be comprised of a single electrode pair, or an array of multiple electrode pairs operated in parallel. Where current is applied to the system, it is capable of more effectively operating in an anaerobic environment. With the presence of oxygen minimized, the electrons utilized in the oxidation of the targeted substance, particularly BOD, will be deposited on the electrode. This can improve the accuracy of the signal produced. A similar principle applies to other potentially competitive electron acceptors, such as nitrate, and, as such, the minimization of their respective concentrations will improve the responsiveness of the signal. For example, a denitrification and/or nitrification step prior to entry into the sensor may be advantageous.

In one embodiment, the invention comprises two biological electrodes with a voltage applied between the electrodes (creating an anode and cathode). No membrane is needed to separate the electrode pair. At a fixed applied voltage, the current in the system will vary as a function the concentration of complex organic compounds (such as VFAs) in the solution. In this embodiment, the anode will oxidize acetate and volatile fatty acids (VFAs). The cathode can reduce other species, such as $CO_2$, to methane.

Figure 4B:
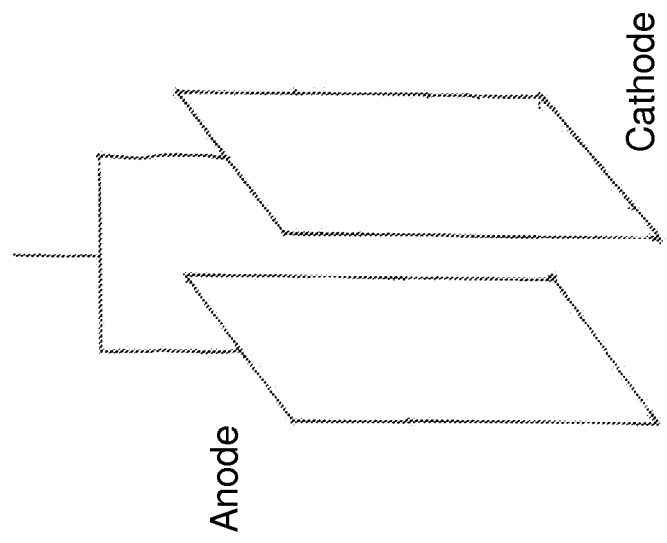
FIG. 4B depicts an embodiment of a bioelectrochemical system for use in a VFA sensor.
Figure 4A:
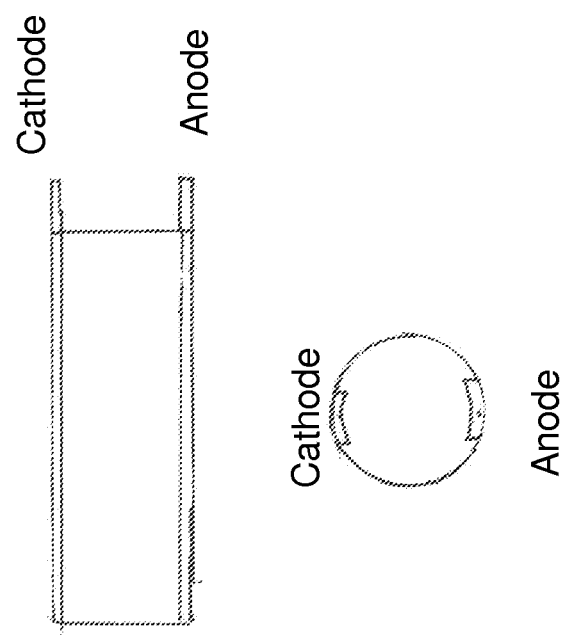
FIG. 4A depicts an embodiment of a bioelectrochemical system for use in a VFA sensor.

Exemplary embodiments of BES cells for use as a VFA sensor, e.g., without a membrane are shown in FIGS. 4A and 4B. The cells may be two substantially parallel electrodes (FIG. 4B) or the cells may comprise a tube with the electrodes disposed within the tube (FIG. 4A). When arranged at the end of a flow tube, the cell depicted in FIG. 4A provides the additional benefit of substantially allowing all oxygen to be consumed prior to reaching the electrodes. Thus an anaerobic environment is provided, wherein a greater proportion of the electrons created during the metabolic oxidation of organics will be deposited to the electrode.

In a second embodiment, a control cathode can be used, leaving only the bio-anode as the active agent. This control cathode can be refilled or replaced in the event of exhaustion.

Bacteria

A wide range of electrically active microbes can be incorporated into BESs to achieve the desired response and sensitivity. Generally, the electrically active microbe is a species selected from the genera *Bacillus, Geobacter, Shewanella, Clostridia, Pseudomonas, Desulfovibrio, Desulfuromonas, Desulfobulbus, Rhodoferax*, or *Escherichia*. Combinations of microbe species may also be used with the systems, sensors, and methods of the invention. By selecting desired traits in electrically active microbes or encouraging the natural selection of superior microbes, BESs which are specific for certain chemical species, e.g., VFAs, can be developed. Additionally, microbes which are best suited for certain process conditions, such as hydrolysis, fermentation, or oxidation of organic compounds, can be used to populate the BES. Thus, a robust chemical sensor will have a variety of microbes, each playing a role in metabolizing a particular compound or set of compounds. For example, *Geobacter sulfurreducens* has been shown to actively metabolize VFAs, especially in the presence of metals which can receive electrons generated in the process.

The invention encompasses BESs having mixed cultures of electrically active microbes in one or more cells or having a plurality of cells, wherein each cell has a separate or a different microbial population. Sensors having an array of cells, each with a separate microbial population may be used, for example, to perform multiplex analysis on a sample, e.g., simultaneously measuring for BOD and other species, e.g., nitrates, or to measure BOD and its component parts, e.g., VFAs and hydrocarbons, separately.

Controlling Specificity

For the detection and monitoring of VFAs and other specific organics, the invention may use a pure or substantially pure culture of an exoelectrogenic microbe community characterized by its limited metabolic versatility. Such sensors will be useful where process conditions are governed by the production of specific by-products, or a user is obligated to report levels of species beyond BOD measurements. The limited metabolic versatility is such that exoelectrogens are capable of utilizing only the substance targeted as an electron donor. The preferred microbe community will be able to utilize only acetate or hydrogen as electron donors, such as *Geobacter sulfurreducens* isolates. The metabolic inflexibility of *G. sulfurreducens* is similar to that of other methanogenic microbe species which typically utilize acetate and/or hydrogen as electron donors and carbon dioxide as a carbon source. Thus, *G. sulfurreducens* may become the basis for a sensor for a specific species, e.g., VFAs, as discussed below. Of course, the system could also be developed using other species or a mixed exoelectrogenic community which has been optimized such that the metabolic characteristics of each component species indicate the relative concentration of volatile fatty acids present in the waste stream.

A sensor employing a specific microbial community, such as *G. sulfurreducens*, may be calibrated and used to control a specific process, for example an anaerobic digester. The signal could be compared against a simulation model of anaerobic digestion activity. This model can include both expected VFA concentration as a function of various parameters (temperature, pH, salinity) as well as specific failure modes. The bioelectrochemical signal could also be used in a process control system, optimizing system performance and highlighting potential system imbalances at an early stage. High or low concentrations of acetic acid and additional VFAs (indicating system imbalance) would be rapidly detected and the system controls would be adjusted to remove the threat of reactor instability. Bioelectrochemical systems could be deployed at influent/effluent ports as well as internally throughout the anaerobic reactor itself. The signal generated from each sensor could also be used to predict optimal system parameters including hydraulic retention times, chemical oxygen demand loading rates, temperature, or pH for the digester.

Calibration and Measurement of BOD

Figure 5:
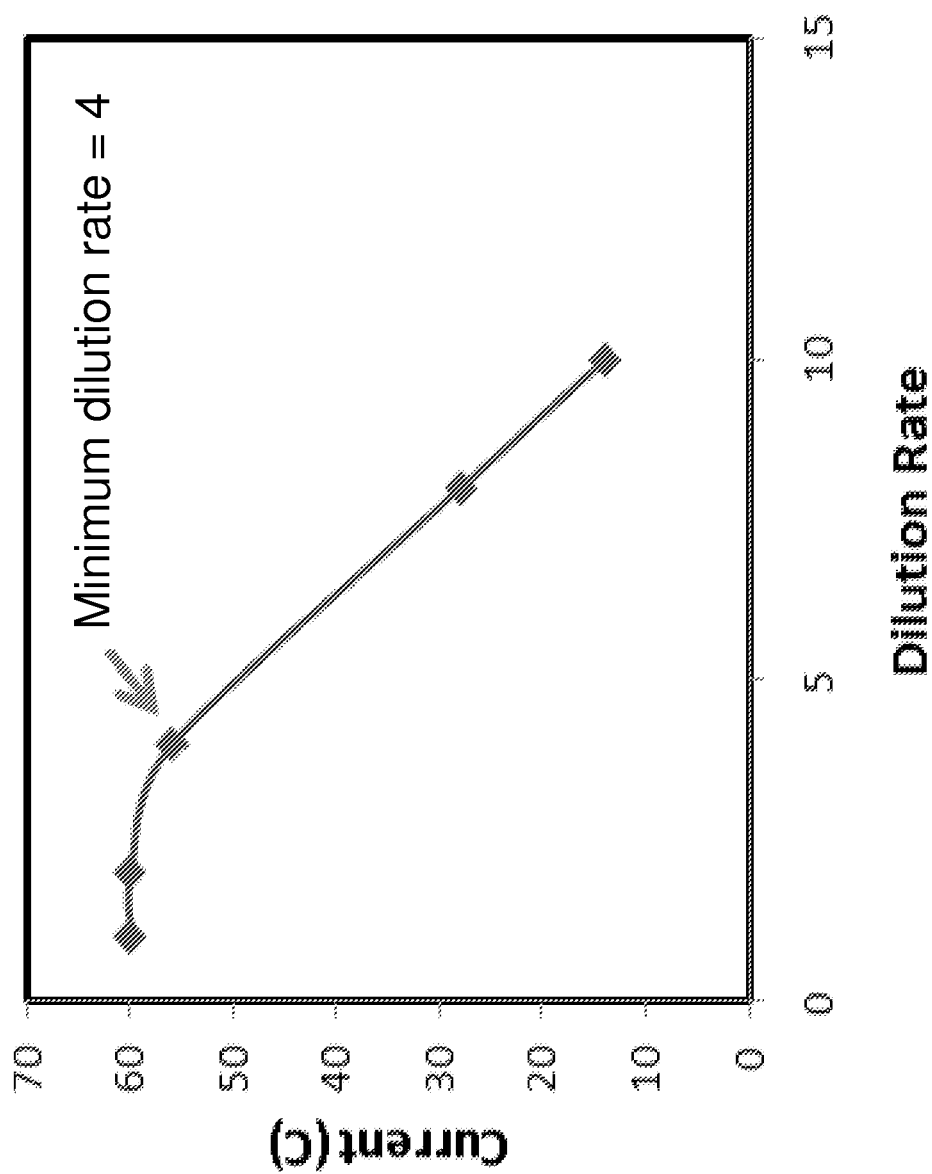
FIG. 5 shows a dilution curve used to determine an effective operational range of a BOD sensor.
Figure 6:
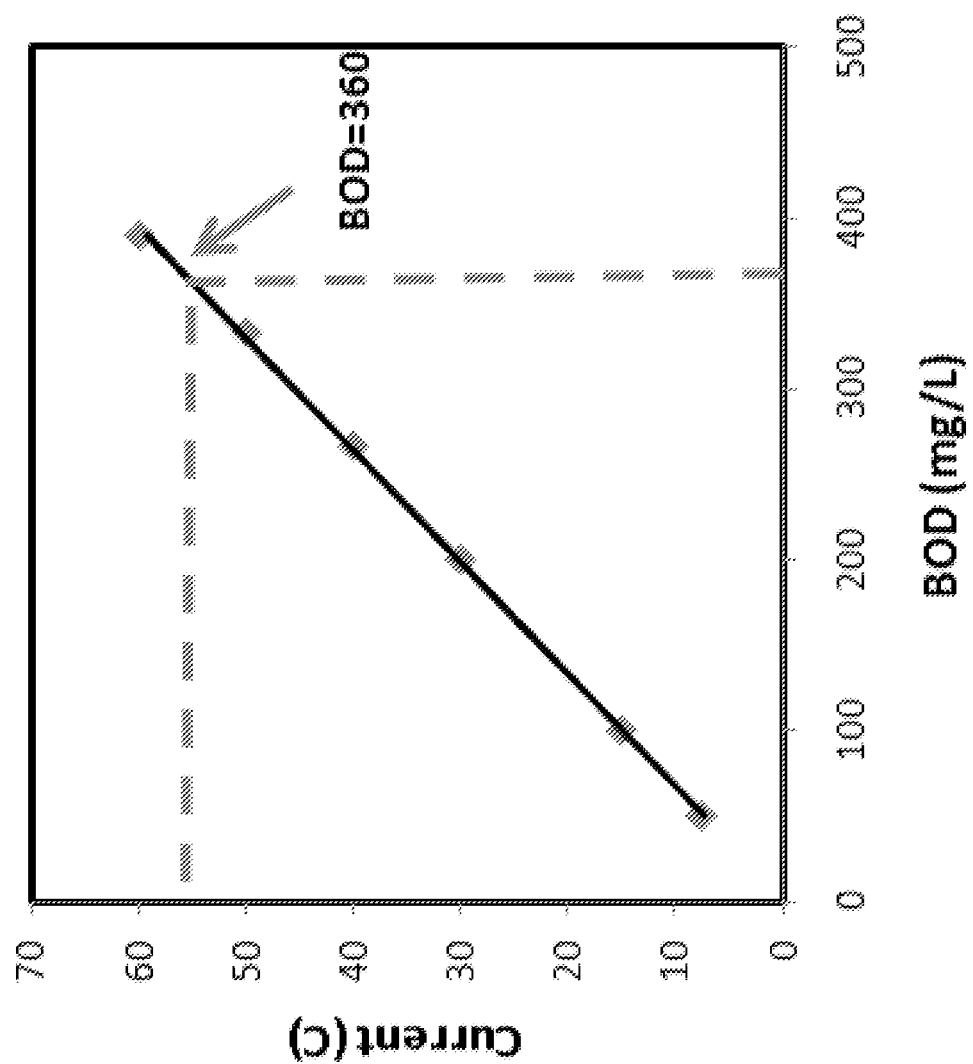
FIG. 6 shows the correlation between BOD and current for a BOD sensor.

Regardless of the arrangement of the BOD detection systems or the culture of bacterial used to populate the sensors, a cell will have to be calibrated or otherwise characterized prior to becoming the basis for a BOD sensor. As shown in FIGS. 5 and 6, the current produced by a cell will be measured and compared against the known values of the current produced by various BOD levels at the dilution level of that cell. First, as shown in FIG. 5, a minimum dilution rate for accurate BOD analysis for that cell will be determined. In other words, at dilution rates less than the minimum dilution rate, the cell may be saturated, and the corresponding current measurement has less precision than a current measurement in the linear region, e.g., at a dilution greater than the minimum dilution rate.

Having determined the minimum dilution rate, the cell can be calibrated by exposing the cell to a number of standardized BOD samples, and measuring the current to construct a correlation, e.g., as shown in FIG. 6. While FIG.

6 correlates BOD with current, it is also possible to correlate BOD with potential, e.g., across a resister of known value. The correlation shown in FIG. 6 may be programmed into a processor used with a system of the invention, or an operator may use the correlation to interpret BOD values from measurements of the multimeter. The correlation may be expressed as a mathematical correlation, or it may be prepared in a "look-up" table wherein values between points are assumed to be approximately linear in value between calibration points.

Having calibrated each cell for a value of BOD corresponding to current, etc., the cells may be incorporated into a system of the invention. Because each cell may be easily identified as operating in its correlated (linear) range, or saturated, or below threshold, meaningful measurements can be quickly and accurately collected corresponding to at least one sensor operating in its correlation range. This will allow for a wider range of BOD values which can be accurately measured and will allow for a faster response time for the measurement.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

The invention claimed is:

1. A system for measuring a biological oxygen demand of a fluid, comprising
    a bioelectrochemical system comprising a housing for first and second electrodes and a culture of exoelectrogenic bacteria, wherein the housing limits aerobic metabolism in proximity to the first electrode and the second electrode and the electrodes are configured to operate under anaerobic conditions;
    a buffer storage system;
    an electric current or voltage sensor operably coupled to the bioelectrochemical system; and
    control electronics operably connected to the current or voltage sensor and the buffer storage system, and capable of receiving a measurement from the current or voltage sensor and causing the buffer storage system to contact the sample with a buffer.

2. The system of claim 1, wherein the culture of exoelectrogenic bacteria comprises a species selected from the genera *Bacillus*, *Geobacter*, *Shewanella*, *Clostridia*, *Pseudomonas*, *Desulfovibrio*, *Desulfuromonas*, *Desulfobulbus*, *Rhodoferax*, or *Escherichia* or combinations thereof.

3. A method for determining a biological oxygen demand (BOD) of a sample, comprising:
    diluting the sample with a dilution fluid to obtain at least three different dilutions of the sample;
    measuring the BOD of each of the at least three different dilutions using a bioelectrochemical system to obtain at least three BOD values; and
    comparing the at least three BOD values to determine a BOD of the sample; and
    determining a minimum dilution rate to enhance accuracy.

4. The method of claim 3, wherein measuring the BOD of each of the at least three different dilutions comprises correlating a current or voltage measurement to a BOD value.

5. The method of claim 3, wherein at least five different dilutions of the sample are obtained and measured for BOD.

6. The method of claim 3, wherein the method is completed in less than 1 hour.

7. The method of claim 3, further comprising determining whether one or more cells in the bioelectrochemical system is operating in a linear range, saturated, or below threshold, and collecting measurements in the linear range.

8. The method of claim 5, further comprising determining whether one or more cells in the bioelectrochemical system is operating in a linear range, saturated, or below threshold, and collecting measurements in the linear range.

9. A sensor for determining the presence of targeted organic compounds, comprising:
    first and second electrodes, configured to operate under anaerobic conditions;
    a voltage source operably coupled to the first and second electrodes and configured to provide a voltage;
    a current sensor operably coupled to the first and second electrodes and capable of measuring a current between the first and second electrodes;
    a culture of exoelectrogenic bacteria for metabolically utilizing the targeted organic compounds as an electron donor; and
    a housing for the first and second electrodes, wherein the housing limits aerobic metabolism in proximity to the first electrode and the second electrode.

10. The sensor of claim 9, wherein the culture comprises *Geobacter sulfurreducens*.

11. The sensor of claim 9, wherein the targeted organic compounds comprise a volatile fatty acid.

12. The sensor of claim 9, further comprising a processor operably connected to the current sensor, capable of receiving a value of current and determining a value of biological oxygen demand from the value of current.

13. The sensor of claim 12, wherein the sensor is operable to output a signal to a process control system for optimizing performance of an anaerobic system, the system comprising an anaerobic digester, and the processor is operably connected to the process control system and capable of initiating changes in the operation of the anaerobic digester in response to changes in the current.

14. The sensor of claim 9, wherein one of the first or second electrodes comprises stainless steel.

15. A sensor for determining the presence of targeted organic compounds, comprising:
    first and second electrodes, configured to operate under anaerobic conditions;
    a voltage source operably coupled to the first and second electrodes and configured to provide a voltage;
    a current sensor operably coupled to the first and second electrodes and capable of measuring a current between the first and second electrodes;
    a culture of exoelectrogenic bacteria for metabolically utilizing the targeted organic compounds as an electron donor, wherein the current resulting from the metabolization of the targeted organic compounds determines the presence of the targeted organic compounds; and a housing for the first and second electrodes, wherein the housing limits aerobic metabolism in proximity to the first electrode and the second electrode.

16. A electric current or voltage sensor for determining the presence of targeted organic compounds, comprising:

first and second electrodes, configured to operate under anaerobic conditions;

a voltage source operably coupled to the first and second electrodes and configured to provide a voltage;

a current sensor operably coupled to the first and second electrodes and capable of measuring a current between the first and second electrodes;

a culture of exoelectrogenic bacteria for metabolically utilizing the targeted organic compounds as an electron donor, wherein such metabolic activity of the exoelectrogenic bacteria is specific for the targeted organic compounds; and a housing for the first and second electrodes, wherein the housing limits aerobic metabolism in proximity to the first electrode or the second electrode.

17. The system of claim 1, wherein the sensor is configured to determine a minimum dilution rate to enhance accuracy.

18. The sensor of claim 9, wherein the sensor is configured to determine a minimum dilution rate to enhance accuracy.

19. The sensor of claim 9, wherein the sensor, further comprises:

a buffer chamber.

* * * * *